United States Patent [19]
Chuang et al.

[11] Patent Number: 5,196,495
[45] Date of Patent: Mar. 23, 1993

[54] HAIR FIXATIVE POLYMERS

[75] Inventors: Jui-Chang Chuang, Wayne; Edward W. Walls, Jr., Cranford, both of N.J.; Stephen C. Johnson, Singapore, Singapore

[73] Assignee: ISP Investments Inc., Wilmington, Del.

[21] Appl. No.: 653,207

[22] Filed: Jan. 25, 1991

[51] Int. Cl.$^5$ ............................................... C08F 26/10
[52] U.S. Cl. .................................. 526/264; 526/303.1; 526/319
[58] Field of Search .................. 526/264, 303.1, 319; 424/71, 47, 78.18, 78.31, 78.33

[56] References Cited

U.S. PATENT DOCUMENTS 4,859,455  8/1989  Nowak, Jr. et al. .................. 424/47

Primary Examiner—Joseph L. Schofer
Assistant Examiner—Alex H. Walker
Attorney, Agent, or Firm—Walter Katz; Jules Goldberg; Joshua J. Ward

[57] ABSTRACT

A hair spray fixative resin comprises a vinyl acetate/alkyl maleate half ester/N-substituted acrylamide terpolymer in a molar ratio of about 1.0 to 0.6–0.8 to 0.08–0.12, which is preferably produced by a suspension or solution polymerization process. Utilizing N-substituted acrylamides in place of isoborneol methacrylates in the terpolymer provides superior holding power over conventional hair fixative resins, at lower cost.

4 Claims, No Drawings

HAIR FIXATIVE POLYMERS

TECHNICAL FIELD

This invention relates to an improved hair spray resin, adapted for use in aerosol and pump formulations, and having excellent hair holding capability under conditions of high humidity, and having superior compatibility with aqueous, hydroalcoholic, and alcohol solvents, hydrocarbon or other type propellants.

BACKGROUND OF THE INVENTION

Effective hair spray formulations and film forming resins must meet a rigid set of requirements. Specifically, the film forming resins should remain non-tacky in a humid environment but be easily removed using soap solutions such as shampoos. The film should have high hair cohesivity and posses sufficient strength and elasticity so as to avoid dusting or flaking when the hair is subjected to combing or brushing stresses, and remain clear, transparent and glossy on aging. The film forming resin should have a viscosity range which permits spraying without nozzle clogging, and should show little or no tendency to interact with perfumes or other optional components typically utilized in a hair spray formulation. The resin should also be readily soluble in various solvents while exhibiting good compatibility with conventional propellants such as hydrocarbon propellants, dimethyl ether propellants, or mixtures thereof.

Many polymeric systems have been developed in an attempt to meet these stringent requirements. Among these are polyvinylpyrrolidone and co-polymers of N-vinylpyrrolidone with vinyl acetate. However, these co-polymers do not exhibit the desired degree of holding under high humidity conditions. Moreover, several of the vinylpyrrolidone polymers possess an unpleasant odor. Methyl vinyl ether/maleic acid half ester co-polymers have also been used in hair sprays but must be of a relatively high molecular weight to achieve adequate holding. Vinyl acetate polymers having 15 to 35 percent of their acetate groups converted to hydroxyl groups have been proposed for increased solubility in carbon dioxide propellant systems. However such increased solubility is achieved at the cost of lowered holding power. While each of the above resins meets at least some of the above cited requirements, none exhibits all of these characteristics to a satisfactory degree.

In U.S. Pat. No. 4,689,379, a terpolymer resin of random or alternating structure is discussed comprising essentially a vinyl ester, a water insoluble or water miscible alkyl maleate half ester and the acrylate or methacrylate ester of a saturated hydroxylated bicyclic hydrocarbon in a molar ratio of about 1 to 0.35-1 to 0.05-0.25. Preferably, the resin is prepared in the form of beads or microspheres by suspension polymerization to provide a higher molecular weight for better hair holding under humid conditions. The terpolymers are preferably composed of vinyl acetate, an alkyl maleate half ester and acrylate and/or methacrylate esters of isoborneol, exo-norborneol and endonorborneol, with the isoborneol ester most preferred.

While useful in the preparation of hair treating formulations and hair sprays, additional advances in the art continue to be sought.

SUMMARY OF THE INVENTION

It is an object of the present invention to provide hair fixative polymers which provide at least the same desired performance characteristics as exhibited by the known terpolymers yet have additional holding power under high humidity conditions.

It is another object to provide hair fixative polymers which provide additional curl retention yet are more economically produced than previous formulations.

It is yet another object to provide a hair fixative polymer which has superior propellant compatibility, removability and hair holding properties.

These and other objects of the present invention are achieved by providing a terpolymer resin comprising a vinyl ester, a water insoluble or water miscible alkyl maleate half ester, and an N-substituted acrylamide. Preferably, the N-substituted acrylamide is N-t-butyl acrylamide, N-t-octyl acrylamide or N-[1-(2-pyrrolidonyl)ethyl]acrylamide, added in an amount of less than 25% by weight.

DETAILED DESCRIPTION OF THE INVENTION

The present invention is directed to a terpolymer resin of random or alternating structure comprising a vinyl ester, a water insoluble or water miscible alkyl maleate half ester, and an N-substituted acrylamide.

The proportions of monomers in the present resin are critical since, above 3.5:1, vinyl acetate to maleate half ester, the terpolymer becomes insoluble in commercial alcohol carriers such as ethanol and below 1:1, the terpolymer develops tact. Also, the high water sensitivity and/or low glass transition temperatures of the vinyl ester and maleate half ester co-polymers prevent their synthesis by an economical one step suspension polymerization process. Previously it had been thought that the incorporation of an acrylate or methacrylate ester of a saturated hydroxylated bicyclic hydrocarbon, which forms a homopolymer of relatively high glass transition temperature (Tg), was an essential monomer in the terpolymer. However, it has since been discovered that N-substituted acrylamide may be substituted for the acrylate and/or methacrylate ester to synthesize terpolymers by a suspension polymerization process and still yield a hair spray formulation which exhibits the desired properties of curl retention, removability and hair holding, with superior compatibility to aqueous, hydroalcoholic and alcohol solvents, as well as hydrocarbon or other type propellants.

It has also been discovered that an N-substituted $C_3-C_{12}$ alkyl acrylamide, preferably having a lactam ring containing alkyl, may be substituted for the acrylate or methacrylate ester mentioned above to synthesize terpolymers by a solution polymerization process and yield a hair spray resin with the desired characteristics. Such a method was previously considered infeasible.

Compounds illustrative of the N-substituted acrylamides usable with this invention include N-t-butyl acrylamide, N-t-octyl acrylamide, and N-[1-(2-pyrrolidonyl)ethyl]acrylamide (PEAM). PEAM is particularly adaptable for use in the solution polymerization process. Preferably, N-substituted $C_3-C_{12}$ acrylamides are used. Compounds usable with the present invention include N-isopropyl acrylamide, N-n-butylacrylamide, N-isobutyl acrylamide, N-t-butylacrylamide, N-s-amylacrylamide, N-s-isoamylacrylamide, N-t-amylacrylamide, N-

(1,1-dimethylbutyl)- acrylamide, N-(1-methyl-1-ethylpropyl)acrylamide, N-(1,1,2-trimethylpropyl)acrylamide, N-cyclohexylacrylamide, N-n-heptylacrylamide, N-(1,1-dimethylamyl)acrylamide, N-(1-methyl-1-ethylbutyl)acrylamide, N-(1,1-diethylpropyl)acrylamide, N-(1-methyl-1-ethyl-2-methylpropyl)acrylamide, N-(1,1,2-trimethylbutyl)acrylamide, N-(1,1,3-trimethylbutyl)acrylamide, N-n-octylacrylamide, N-t-octylacrylamide also known as N-(1,1,3,3-tetramethylbutyl)acrylamide, N-(1,1-dimethylhexyl)acrylamide, N-(1,1-diethylbutyl)acrylamide, N-(1-methyl-1-propylbutyl)acrylamide, N-(1,1,4-trimethylamyl)acrylamide, N-(1,4-dimethyl-1-ethylamyl)acrylamide, N-(1,3-dimethyl-1-ethylbutyl)acrylamide, N-(1,1-dimethylheptyl)acrylamide, N-(1-methyl-1-propylamyl)acrylamide, N-(1,1-diethylamyl)acrylamide, N-n-dodecylacrylamide, N-[1-(2-pyrrolidonyl)ethyl]acrylamide and the like.

The molar ratio of vinyl ester to the N-substituted acrylamide should be between about 4:1 and 20:1, with 10:1 preferred. Over 25%, the terpolymer may become heat sensitive, or discolored, and solubility may be affected. A particularly preferred molar ratio of vinyl acetate/mono-n-$C_4$ to $C_5$ alkyl maleate/N-substituted acrylamide is about 1:0.6–0.8:0.08–0.12 and more preferably 1:0.75:0.1.

Compounds illustrative of the water insoluble or water miscible alkyl maleate half ester monomers of this invention are the propyl, butyl, pentyl, hexyl, heptyl, octyl, nonyl and decyl half esters; although the n-butyl, sec-butyl, isobutyl, and n-pentyl half ester monomers are the most preferred.

Examples of the vinyl ester monomeric component are those containing 4 to 14 carbon atoms which include vinyl acetate, vinyl propionate, vinyl isopropionate, vinyl isobutyrate, vinyl butyrate, vinyl hexanoate, vinyl pivalate, vinyl laurate and vinyl neodecanoate, of which vinyl acetate and vinyl propionate are the most preferred.

The present resin may be prepared by suspension or solution polymerization, but suspension polymerization provides an advantage as the resin is obtained in the form of beads or microspheres. The terpolymer resin obtained by either process has a higher molecular weight for better hair holding under humid conditions and achieves the highest conversion, thus minimizing unreacted monomers. When the resin is in dry bead form, it can be handled and shipped safely in the absence of flammable alcohol solvents.

When synthesized by the suspension polymerization process, the microspheres of the terpolymeric resin generally have an average diameter of between about 0.5 and about 2.5 mm. The polymer products produced by either suspension or solution polymerization possess a relative viscosity (RV), measured at 1 g per 100 ml ethanolic solution at 25° C., in the range of 1.2–2.0.

Generally, the suspension polymerization process comprises adding the monomers, individually or premixed in the above proportions, to a 0.1 to 2.0% by weight aqueous suspension medium, preferably a 0.25 to 1.0 weight % solution, of a carboxylated polyelectrolyte, preferably methyl vinyl ethermaleic acid copolymer (GANTREZ® S-95 or S-97 produced by GAF Chemicals Corp.), wherein they are polymerized in the presence of a free radical initiator under conditions of agitation at a temperature of between about 40° and about 90° C., preferably between about 50° and about 70° C. The initiator can be added to the monomer mixture before or after the monomers have been charged into the suspension medium. The reaction is undertaken in an inert atmosphere which can be maintained by purging with nitrogen to eliminate oxygen.

The polymerization reaction is carried out under constant agitation over a period of from about 4 to about 12 hours; typically 6 to 8 hours is sufficient to complete the reaction and form a bead-like terpolymer product. The beads are then separated from the suspension medium, washed with water, and dried. The supernatant liquid separated from the product can be recycled to the reaction zone if desired as a make-up suspension media in which any unreacted monomer in the supernatant liquid can be converted, thus providing a highly efficient, pollution-free process.

Generally, the suspension medium can be any aqueous solution containing from about 0.1 wt. % to about 2.0 wt. % of a carboxylated polyelectrolyte suspending agent. Suitable suspending agents include methyl- vinyl ether/maleic acid copolymer, i.e. GANTREZ® S-95 or S-97; ethylene/maleic anhydride copolymer such as EMA resin supplied by Monsanto Co.; vinyl acetate/maleic anhydride copolymer, N-vinyl-2-pyrrolidone/maleic anhydride co-polymer and N-vinyl-2-pyrrolidone/acrylic acid copolymer. The concentration of total monomers in the suspension medium can vary from about 10 to 50 wt. %. However, concentrations of between about 20 and about 40 wt. % are recommended as being the most economical.

Generally, between about 0.05 and about 5.0 wt. % initiator, based on total monomers of the terpolymer, can be employed in the polymerization reaction although, in most instances, between about 0.1 and about 2.0 wt. % initiator is sufficient to promote the reaction.

The free radical initiators employed in the present reaction are typically low temperature initiators having a half-life of 10 hours at temperatures between about 45° and 65° C., although any of the free radical initiators which are effective at temperatures between about 30° C. and about 80° C. are suitably employed herein. Typical low temperature initiators include peroxyesters such as t-butylperoxypivalate (Lupersol® 11) and t-butylperoxyneodecanoate (Lupersol® 10), peroxydicarbonates such as di-(n-propyl)peroxydicarbonate (Lupersol® 221), di-(sec-butyl)peroxydicarbonate (Lupersol®225) and di-(2-ethylhexyl)peroxydicarbonate (Lupersol® 223) all supplied by Atochem Corporation. Also, azo initiators such as 2,2'-azobis(2,4-dimethylvaleronitrile) (VAZO®-52) and 2,2'-azobis(2,4-dimethyl-4-methoxyvaleronitrile) (VAZO®-33W), both supplied by DuPont, are suitable. Of course, other initiators may also be used.

The inventive terpolymer resins can also be produced by a solution polymerization process. The various monomers are added to an organic solvent such as acetone, along with an initiator as previously described. The monomers may be premixed, or added individually to the solvent. If premixed, the monomers should be in a concentration of about 50–70%. If the monomer mixture becomes too thick during polymerization, additional solvent could be added. The initiator causes the monomers to polymerize and form the terpolymer. Preferably, polymerization occurs during agitation in a reaction zone maintained at a temperature between about 30° C. and 90° C., until the reaction is complete. After completion, the terpolymer is removed from the organic solvent by a solvent exchange process, i.e. exchanging the organic solvent for an alcohol such as ethanol. This may be done by distillation, solvent extraction or other means. The organic solvent may be reused after recovery. By varying the solvent to monomer ratio, the relative viscosity (RV) of the product can be adjusted. For example, a 50% monomer concentration may yield a RV of 1.3, a 70% concentration a RV of 1.5 and a 25% concentration, a RV of 1.05. The solution polymerization process is somewhat longer than the suspension process, taking typically from 12-16 hours.

The present terpolymeric resins are employed as the active ingredients in any of the standard hair treating formulations employed for pump and aerosol sprays. The resins can also be used to augment existing hair spray formulations to improve solubility, hair holding and propellant compatibility. When used as the sole active hair holding agent in the formulation, the present resins are employed in concentrations between about 0.5% and about 18%, preferably between about 1.0% and about 5.0% for aerosol and between about 4 and about 12% for pump sprays.

In preparing the hair treatment formulations, the resin is usually dissolved in an inert carrier, such as a lower alcohol, e.g. ethanol, an aqueous ethanol solution, isopropanol or the like. For aerosol sprays, the formulations may also include a conventional propellant such as, for example, a 20/80 blend of propane/isobutane (Propellant A-46), dimethyl ether, nitrogen, nitrogen oxide, carbon dioxide, or mixtures thereof.

The formulations are charged into a canister and the propellant pressurized into the canister to provide a spray operated through a pressure release nozzle. The present resins have a long shelf life and avoid nozzle clogging or canister corrosion when employed in the above concentrations.

Having thus generally described the invention, reference is now had to the following examples which provide specific and preferred embodiments but which are not to be construed as limiting the scope of the invention as more broadly described above and in the appended claims. All parts given are by weight unless otherwise indicated.

EXAMPLE 1

This example illustrates the preparation of vinyl acetate/mono-n-butyl maleate/t-butylacryamide terpolymer resin by the suspension polymerization process.

Into a four-necked, one-liter resin kettle, fitted with a mechanical agitator, a reflux condenser, a dropping funnel/thermometer, and a nitrogen inlet tube was charged:

34.40 g of vinyl acetate (VAC, 0.40 mole);
51.60 g of mono-n-butyl maleate (MBM, 0.30 mole);
2.54 g of t-butyl acrylamide (BAM, 0.02 mole); and,
1.1805 g of di-(2-ethylhexyl) peroxidicarbonate (LUPERSOL ™ 223M, 75% active).

The contents of the kettle were mixed thoroughly by the mechanical agitator operating at about 250 rpm for a period of 5 minutes, after which a polyelectrolyte solution, prepared from 0.5097 g of GANTREZ ™ S-95 and 177.1 g of distilled water, was added.

The mixture was purged with nitrogen and gently heated to 60° C. over a period of 60 minutes while maintaining agitation and the nitrogen purge. The reactants were held at 60°-62° C. for four hours and then at 64°-66° C. for four hours during which a bead-like resin product was formed. The mixture was cooled to 15° C. in a water/ice bath and the supernatant liquid decanted. The remaining beads, having an average diameter of 0.5-1.0 mm., were washed twice with distilled water, filtered and then dried under vacuum overnight at ambient temperature, followed by drying in a hot air oven at 55°-60° C. for 24 hours.

The supernatant liquid separated from the resin product may be recycled to the reaction zone to provide a portion of the suspension medium, if desired.

The terpolymeric product, referred to hereafter as Polymer 1, was recovered in a yield of 84.3%, in the form to microspheroidal particles having the following composition:

38.85% vinyl acetate (VAC);
58.28% mono-n-butyl maleate (MBM);
2.87% t-butylacrylamide (BAM).

Polymer 1 has a relative viscosity of 1.505, a K-value of 43.6 and an acid number of 153.2 mg NaOH/g of resin.

EXAMPLES 2-8

In Examples 2-8, a procedure identical to that described in Example 1, with the below modification, was repeated to prepare Polymers 2-8.

Example 2-4 were modified in that the weight ratios of the monomers were altered as shown in Table 1. In examples 5,6, t-butylacrylamide, (BAM), was replaced by t-octylacrylamide (OAM) and the weight ratios of the monomers were also altered. In Examples 7-8, t-butylacrylamide was replaced by a mixture of t-buylacrylamide and t-octylacrylamide and the weight ratios of the monomers were also altered. In all experiments, GANTREZ ™ S-95 concentration in water was 0.33% and LUPERSOL ™ 223M75 concentration was 1.0% based on the total monomer weight. Each of the polymeric products, i.e., Polymers 1-8, were analyzed as reported in the following Table I.

TABLE 1

| Polymer | 1 | 2 | 3 | 4 | 5 | 6 | 7 | 8 |
|---|---|---|---|---|---|---|---|---|
| Vinyl Acetate (VAC) | 38.85 | 38.30 | 37.76 | 37.24 | 41.44 | 36.15 | 36.09 | 37.31 |
| Mono-n-butyl Maleate (MBM) | 58.28 | 57.45 | 56.65 | 55.87 | 49.73 | 54.22 | 54.13 | 55.97 |
| N-t-Butyl-acryl-amide (BAM) | 2.87 | 4.25 | 5.59 | 6.89 | — | — | 4.02 | 2.75 |
| N-t-octyl-acryl-amide (OAM) | — | — | — | — | 8.83 | 9.63 | 5.76 | 3.97 |
| Relative Viscosity | 1.505 | 1.510 | 1.648 | 1.519 | 2.010 | 1.710 | 1.694 | 1.825 |
| K-Value | 43.6 | 43.8 | 49.1 | 44.0 | 59.4 | 51.2 | 50.6 | 54.6 |

TABLE 1-continued

| Polymer | 1 | 2 | 3 | 4 | 5 | 6 | 7 | 8 |
|---|---|---|---|---|---|---|---|---|
| Ethanol Solubility | GOOD | GOOD | GOOD | GOOD | GOOD | GOOD | GOOD | GOOD |

EXAMPLE 9

This example illustrates the preparation of vinyl acetate/mono-n-butyl maleate/t-octyl acrylamide terpolymer in acetone by a solution polymerization process, followed by exchanging acetone with ethanol.

Into a four-necked, one-liter resin kettle, fitted with a mechanical agitator, a reflux condenser, a dropping funnel/thermometer, and a nitrogen inlet tube was charged
86.00 g of VAC (1.00 mole);
129.00 g of MBM (0.75 mole);
18.30 g of OAM (0.10 mole); and,
100.0 g of acetone.

The contents of the kettle were mixed by a mechanical agitator operating at about 250 rpm, purged with nitrogen and heated to 57°-58° C. over a period of 30 minutes. LUPERSOL TM 223M75 initiator (0.2188 g) was added hourly for a total of 20 additions. At this point, the residual vinyl acetate content was about 1.2% based on titration. 116.7 g of anhydrous ethanol were then added and a mixture of acetone and ethanol was removed by distillation. This step was repeated three times and the final distillation temperature was 78°-80° C. The terpolymer solution in ethanol thus obtained had a solids content of 50.7% and an acetone content below 1.0% based on GC analysis.

The terpolymeric product in ethanol, referred to as Polymer 9, has a resin composition as follows:
36.86% VAC;
55.29% MBM;
7.85% OAM.
This polymer has a relative viscosity of 1.395, a K-value of 38.7, and an acid number of 128.9 mg NaOH/g of resin.

EXAMPLES 10-11

In examples 10-11, the procedure described in example 9, was followed with the below noted modifications, to prepare Polymers 10-11.

TABLE II

| Polymer | 9 | 10 | 11 |
|---|---|---|---|
| Vinyl Acetate (VAC) | 36.86 | 37.77 | 36.88 |
| Mono-n-butyl Maleate (MBM) | 55.29 | 56.65 | 55.33 |
| N-t-Butylacrylamide (BAM) | — | 5.85 | — |
| N-t-Octylacrylamide (OAM) | 7.85 | — | — |
| N-[1-(2-Pyrrolidonyl)ethyl] acrylamide (PEAM) | — | — | 7.80 |
| Relative Viscosity | 1.395 | 1.396 | 1.322 |
| K-Value | 38.7 | 38.7 | 34.8 |
| Acid Number | 128.9 | 144.0 | 137.7 |

In examples 10-11, t-octylacrylamide (OAM) was replaced by t-butylacrylamide (BAM) and the weight ratios of the monomers were altered as shown in Table II. In example 11, t-octylacrylamide was replaced by N-[1-(2-pyrrolidonyl)ethyl]-acrylamide (PEAM) and the weight ratios of the monomers were also altered. The monomer concentrations in acetone during polymerization for examples 9-11 were 70, 65, and 65% respectively.

COMPARATIVE EXAMPLE 12

A vinlyacetate/mono-n-butylmaleate/isobornyl acrylate terpolymer with a monomer weight ratios of 36.47:54.71:8.82, as disclosed in example 14 of U.S. Pat. No. 4,689,379, was prepared except ethanol was replaced with acetone to attempt a solution polymerization process and LUPERSOL TM 223 was fed in 16 incremental steps. Acetone was exchanged with ethanol at the end of polymerization. The monomer concentration in acetone during polymerization was 55%. The polymer thus obtained had a relative viscosity of 1.325, a K-value of 35.0, an acid number of 134.4mg NaOH/g of resin and a solids content of 53.3% in ethanol. The terpolymer resin, referred to as Polymer 12, had a higher relative viscosity than the same resin made directly in ethanol.

EXAMPLE 13

This example illustrates the excellent solution properties of the hair spray resins of this invention.

Each resin of examples 1-11 was evaluated for its solubility in ethanol without adding a neutralizing agent such as 2-amino-2-methyl-1-propanol (AMP). In these tests, 2.5 g. of each polymer were dissolved in 67.5 g. of anhydrous ethanol (SDA 40-2 grade) under agitation and the clarity to the solution was noted. For each clear solution, 30 g. of n-hexane were then added and the solubility in ethanol/n-hexane mixture was recorded. In these tests, n-hexane was found to be an ideal substitute for evaluating the compatibility of resin with hydrocarbon propellant A-46 (blend of 20/80 propane/isobutane). The testing results were compared with Resyn ® 28-2930, a vinyl acetate/crotonic acid/vinyl neodecanoate terpolymer commercial hair spray resin available from the National Starch and Chemical Corporation and comparative Polymer 12, as shown in Table III:

TABLE III

| Polymer | Solubility in Ethanol | Solubility in Ethanol/n-Hexane |
|---|---|---|
| Resyn ® 28-2930 (control) | slight | hazy |
| 1 | clear | clear |
| 2 | clear | clear |
| 3 | clear | clear |
| 4 | clear | clear |
| 5 | clear | clear |
| 6 | clear | clear |
| 7 | clear | clear |
| 8 | clear | clear |
| 9 | clear | clear |
| 10 | clear | clear |
| 11 | clear | clear |
| 12 (control) | clear | clear |

In addition, all of the polymers of this invention (polymers 1-11) remained clear in the ethanol/n-hexane mixture at a temperature below −18° C. (0° F.) which is an indication of their excellent compatibility with hydrocarbon propellants for aerosol hair spray applications.

EXAMPLE 14

This example provides a representative formulation for an aerosol hair spray employing a typical hydrocarbon $C_3$–$C_4$ propellant. The resins were each dissolved in anhydrous ethanol, 100% neutralized with 2-amino-2-methyl-1-propanol (AMP) and charged to an aerosol can with a hydrocarbon propellant A-46 (blend of 80/20 propane/isobutane), as noted in following Table IV.

TABLE IV

|  | Formulation A | | Formulation B | |
| --- | --- | --- | --- | --- |
|  | wt. g | wt % | wt. g | wt % |
| Resyn ® 28-2930 (control) | 2.5 | 2.5 | — | — |
| Inventive Hair Spray resin | — | — | 2.5 | 2.5 |
| Anhydrous ethanol (SDA 40-2) | 67.5 | 67.5 | 67.5 | 67.5 |
| Propellant A-46 | 30.0 | 30.0 | 30.0 | 30.0 |
| 2-amino-2-methyl-1-propanol (AMP) | ** | ** | ** | ** |

**As required to 100% neutralization of the carboxyl functionalities of the hair spray resin.

The aerosol hair sprays thus obtained were evaluated for their hair holding properties. Clean, dried tresses were each sprayed with the above formulations for 3 seconds at a distance of 2 inches, combed through twice, rolled with a 158" roller and dried under a salon type drier for one hour. These tresses were then unrolled on a humidity rack and placed in a 80° F., 90% relative humidity cabinet for 90 minutes. The curl readings at 60 and 90 minutes were recorded. The results of the relative curl retention at 60 and 90 minutes intervals, using Resyn ® 28-28930 as the control which is assigned a value of 1.00, are shown in the following Table V. All hair spray resins of the present invention as well as the control deliver the desired fine, dispersed spray pattern without nozzle clogging. A difference of 0.10 or greater represents a significant improvement in hair holding performance.

TABLE V

| Curl Retention Relative to Resyn ® 28-2930 | | |
| --- | --- | --- |
| Hair Spray Resin | 60 minutes | 90 minutes |
| Resyn ® 28-2930 | 1.00 | 1.00 |
| Polymer 1 | 1.45 | 1.50 |
| Polymer 2 | 1.62 | 1.62 |
| Polymer 3 | 1.57 | 1.66 |
| Polymer 4 | 1.71 | 1.92 |
| Polymer 6 | 1.66 | 1.84 |
| Polymer 7 | 1.48 | 1.62 |
| Polymer 10 | 1.20 | 1.28 |
| Polymer 11 | 1.17 | 1.22 |

Table V shows that the vinyl acetate/mono-alkyl maleate/N-substituted acrylamide terpolymers of this invention are significantly superior in high humidity holding (60 and 90 minute intervals at 80° F. and 90% relative humidity) to a commercial hair spray resin such as Resyn ® 28-2930.

After curl retention tests were completed, each of the polymer films were easily removed in aqueous soap solutions or shampoos, leaving no detectable residues.

COMPARATIVE EXAMPLE 15

The following example compares the curl retention of the present resins by solution polymerization with the comparative Polymer 12, under identical polymerization conditions. The curl retention tests of example 14 were repeated and results were summarized below in Table VI.

TABLE VI

| Curl retention relative to Polymer 12 | | |
| --- | --- | --- |
| Hair Spray Resin | 60 minutes | 90 minutes |
| Polymer 12 (control) | 1.00 | 1.00 |
| Polymer 10 | 1.04 | 1.03 |
| Polymer 11 | 1.04 | 1.03 |

Table VI shows that the curl retention of vinylacetate/mono-alkylmaleate/N-substituted acrylamide polymers of this invention are comparable and to some extent are superior to the vinyl acetate/mono-alkyl-maleate/isobornyl methacrylate polymers of U.S. Pat. No. 4,689,379.

This example demonstrates that the hair spray resins of the present invention exhibit excellent water compatibility and thus significantly reduce volatile organic compounds (VOC) in both pump and aerosol hair spray applications.

Hair spray resin, Polymer 1 (3.0 parts), was dissolved in ethanol, (SDA 40-2,15 parts), neutralized with 2-amino-2-methyl-1-propanol (0.51 part) and blended with 81.5 parts of distilled water.

The clear solution thus obtained contains a 50% neutralized resin and is suitable for pump spray applications. When sprayed on the dry, clean tresses, the clear resin solution produced a non-tacky, clear transparent film.

All the products of this invention are noncorrosive to metal or plastic containers and their viscosities remain unchanged over long periods such that nozzle clogging in the normal life of an aerosol or pump dispenser is avoided.

It will be understood by those skilled in the art that other species of vinyl ester, maleate half esters and N-substituted acrylamides can be substituted in the above examples to provide a resin having improved solubility, propellant compatibility and curl retention, and that such substitutions thus fall within the scope of the present invention.

What is claimed is:

1. A terpolymer comprising:
   a. a vinyl ester,
   b. a water insoluble or water miscible alkyl maleate half ester and,
   c. an N-substituted acrylamide which is N-t-butyl acrylamide in a molar ratio of a to b to c of about 1.0 to 0.6–0.8 to 0.08–0.12 and having a relative viscosity in the range of 1.2 to 2.0.

2. The terpolymer of claim 1 wherein the vinyl ester is from the group consisting essentially of vinyl acetate, vinyl propionate, vinyl isopropionate, vinyl isobutyrate, vinyl butyrate, vinyl hexanoate, vinyl pivalate, vinyl laurate, vinyl neodecanoate and mixtures thereof.

3. The terpolymer of claim 1 wherein the N-substituted acrylamide is present in an amount of less than about 25 wt.

4. The terpolymer of claim 1 wherein said alkyl maleate, half ester is from the group consisting of mono-n-butyl maleate, isobutyl maleate, sec-butyl maleate, mono-n-pentyl maleate and mixtures thereof.

* * * * *